United States Patent [19]

Shenoy

[11] 4,089,953
[45] May 16, 1978

[54] 1,5-BENZODIAZOCINES

[75] Inventor: Umakant Devdas Shenoy, London, England

[73] Assignee: DDSA Pharmaceuticals, London, England

[21] Appl. No.: 622,543

[22] Filed: Oct. 15, 1975

Related U.S. Application Data

[63] Continuation-in-part of Ser. No. 487,480, Jul. 11, 1974, abandoned, which is a continuation-in-part of Ser. No. 480,918, Jun. 19, 1974, abandoned.

[30] Foreign Application Priority Data

Jun. 20, 1973  United Kingdom .............. 29274/73

[51] Int. Cl.² .................. A61K 31/44; A61K 31/395; C07D 245/06; C07D 401/04
[52] U.S. Cl. .............................. 424/244; 260/239 BD; 260/294.8 C; 260/294.9; 260/296 B; 260/347.2; 260/347.7; 424/263; 424/285
[58] Field of Search .................... 260/239 BD; 42/244

[56] References Cited

U.S. PATENT DOCUMENTS

| 3,398,159 | 8/1968 | Berger et al. ................ 260/239 BD |
| 3,442,946 | 5/1969 | Keller et al. ................ 260/239 BD |
| 3,466,328 | 9/1969 | Berger et al. ................ 260/239 BD |
| 3,523,939 | 8/1970 | Fryer et al. .................. 260/239 BD |
| 3,751,412 | 8/1973 | Natsugari et al. ............ 260/239 BD |

OTHER PUBLICATIONS

Kuwada et al., Chem. Abstracts, vol. 79, Abstract No. 78860f, (1973).
Kuwada et al., Chem. Abstracts, vol. 80, Abstract No. 96049y, (1974).
Kuwada et al., Chem. Abstracts, vol. 81, Abstract No. 37586u, (1974).
Greenblatt et al., Benzodiazepines in Clinical Practice, (Raven Press, N. Y., 1974), pp. 10-13, 43-44.
Gordon, Psychopharmacological Agents, vol. I, (Academic Press, N.Y., 1964), p. 5.

*Primary Examiner*—Alton D. Rollins
*Attorney, Agent, or Firm*—Burgess, Dinklage & Sprung

[57] ABSTRACT

1,5-Benzodiazocines of the general formula

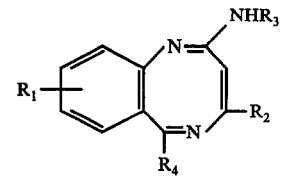

their 5N-oxides, and acid addition salts thereof. In the above formula $R_1$=H, Halogen, $CF_3$, —CN, —NO, $C_{1-6}$ alkyl, $C_{1-6}$ alkoxy or $C_{1-6}$ alkylthio; $R_2$=H, $C_{1-6}$ alkyl or furyl; $R_3$=H, $C_{1-6}$ alkyl, hydroxy-($C_{1-6}$ alkyl), $C_{2-6}$ alkenyl or benzyl; and $R_4$=phenyl, ($C_{1-6}$alkyl)-phenyl, nitrophenyl, halophenyl or pyridyl. Also the production of such compounds from compounds of the benzodiazepine series.

13 Claims, No Drawings

1,5-BENZODIAZOCINES

This application is a continuation-in-part of copending application Ser. No. 487,480, filed July 11, 1974, now abandoned which in turn is a continuation-in-part of Ser. No. 480,918, filed June 19, 1974, now abandoned.

OBJECTS OF THE INVENTION

It is an object of the invention to provide new and useful compounds with the benzodiazocine nucleus for use in human therapy.

It is a further object of the invention to provide a novel synthetic route for compounds with the benzodiazocine nucleus, starting from compounds with the benzodiazepine nucleus, which is capable of commercial application.

The invention relates to 1,4-benzodiazocine derivatives, to methods for their preparation and to therapeutic compositions containing them.

The invention provides 1,4-benzodiazocine derivatives of the general formula I:

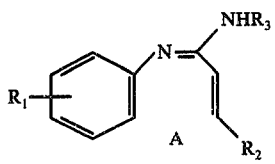

wherein
$R_1$ represents a hydrogen or halogen atom, or a trifluoromethyl, cyano, nitro, lower alkyl, lower alkoxy or lower alkylthio group;
$R_2$ represents a hydrogen atom or a lower alkyl or furyl group;
$R_3$ represents a hydrogen atom, or a lower alkyl, hydroxy (lower alkyl), lower alkenyl or benzyl group; and
—A— represents a grouping of the general formula

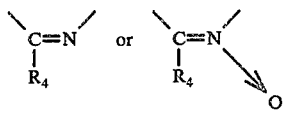

in which $R_4$ represents a phenyl, (lower alkyl) phenyl, nitrophenyl, halophenyl or pyridyl group.

The invention also provides acid addition salts of the above derivatives with pharmaceutically acceptable inorganic or organic acids such as hydrochloric acid, hydrobromic acid, nitric acid, sulphuric acid, acetic acid, formic acid, phosphoric acid, perchloric acid, succinic acid, maleic acid, citric acid and fumaric acid.

As used herein the term "halogen" means fluorine, chlorine, bromine or iodine. The term "lower alkyl" refers to both straight-chain and branched-chain alkyl groups containing from 1 to 6 carbon atoms, for example, methyl, ethyl, n-propyl, isopropyl, n-butyl, n-amyl and n-hexyl. The term "lower alkenyl" refers to both straight-chain and branched-chain alkenyl groups containing from 2 to 6 carbon atoms, for example, vinyl, allyl, butenyl, hexenyl and isobutenyl. The term "lower alkoxy" refers to both straight-chain and branched-chain alkoxy groups containing from 1 to 6 carbon atoms, for example, methoxy, ethoxy and butoxy. The term "lower alkanoyloxy" refers to both straight-chain and branched-chain alkanoyloxy groups containing from 2 to 6 carbon atoms, for example acetoxy, propionyloxy and butyryloxy.

The compounds of the invention have an action on the central nervous system that is in many ways analogous to the corresponding action of known benzodiazepine compounds which are well documented. They also indicate possible anti-inflammatory and diuretic properties. Specifically the compounds of the invention are useful for their psychotropic action on the central nervous system, and for their tranquillizing, sedative and hypnotic properties. For use as tranquillizers they would generally be employed in a dosage between 1 mg and 10 mg depending on the age and condition of the patient. In larger doses they produce sedation, and when the sedative dose is increased a hypnotic effect can be achieved. They can be formulated with adjuvants and excipients as is usual for corresponding benzodiazepine compounds. This invention accordingly provides therapeutic compositions comprising at least one compound according to the invention in admixture with a pharmacologically acceptable diluent or carrier.

Compounds of the general formula I in which $R_2$ represents a hydrogen atom can be prepared according to the invention by treating a compound of the general formula II

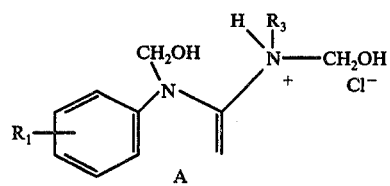

in which $R_1$, $R_3$ and —A— are as above defined, with an inorganic or organic base. Compounds of the general formula II are described and claimed in British patent specification No. 1,359,286 and copending U.S. application Ser. No. 487,479, filed July 11, 1974 now U.S. Pat. No. 4,006,135, entitled Hydroxymethyl Benzodiazepine Derivatives, assigned to the assignee hereof.

Compounds of the general formula II are prepared be reacting a benzodiazepine compound of the general formula

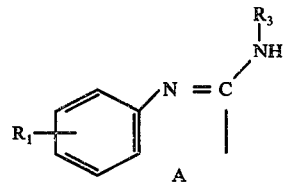

in which $R_1$, $R_3$ and —A— are as above defined, in the presence of HCl, with formaldehyde.

Compounds of the general formula I in which $R_2$ represents a lower alkyl or furyl group may be prepared according to the invention by treating a compound of the general formula III or IV

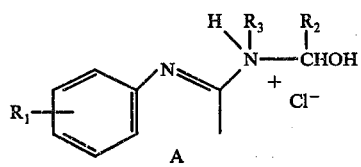

-continued

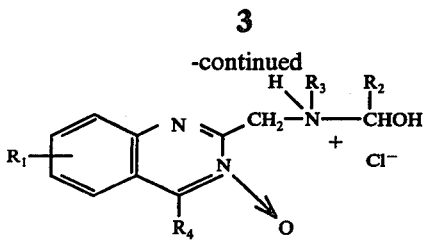

in which $R_1$, $R_3$ and A are as above defined and $R_2$ represents a lower alkyl or furyl group, or an acid addition salt thereof with an inorganic or organic base.

Compounds of the formula III are described and claimed in British patent specification No. 1,359,287 and copending application Ser. No. 487,478, filed July 11, 1974, now abandoned entitled Substituted Hydroxymethyl Benzodiazepine, assigned to the assignee hereof.

Compounds of formula III are prepared by reacting a benzodiazepine compound of the general formula

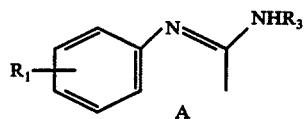

in which $R_1$, $R_3$ and —A— are as above defined, in the presence of HCl, with an aldehyde of the general formula $R_2$—CHO in which $R_2$ represents a lower alkyl or furyl group.

The disclosures of copending U.S. application Ser. Nos. 487,478 and 487,479 are hereby incorporated herein by reference. Compounds of the formula IV are prepared by reacting a benzodiazepine compound of the general formula

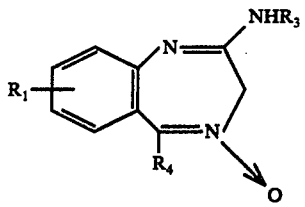

in which $R_1$, $R_3$ and $R_4$ are as above defined, in the presence of HCl, with an aldehyde of the general formula $R_2$—CHO in which $R_2$ represents a lower alkyl or furyl group.

The isomerization involved in each of the above two syntheses, in which the 7-membered ring of the benzodiazepine nucleus is expanded to an 8-membered ring, is completely unexpected and without parallel in the reported literature. Surprisingly, the reaction proceeds smoothly in even mild conditions. The synthesis may be carried out by triturating a compound II, a compound III or a compound IV, hereinafter referred to as the starting material, with a solution of an organic or inorganic base or buffer. Suitable organic and inorganic bases include pyridine, triethylamine, ammonium hydroxide and alkali metal hydroxides, bicarbonates, carbonates and basic ion exchange resins. Suitable organic and inorganic buffers include sodium acetate, ammonium acetate and alkali metal phosphates.

The trituration may be carried out using the starting material in a solid form or in solution in a polar solvent such as methanol, ethanol, propanol, 1,2-dimethoxyethane, dimethylformamide, dimethyl sulphoxide, dioxan, or ethyleneglycoldimethyl ether. When the trituration is carried out in solution the product may be prepcipitated by adding an excess of water. The precipitate may be filtered off, washed with water, and purified by washing with an inert solvent or by crystallization from a suitable solvent.

The synthesis may alternatively be carried out by passing a solution of the starting material III or IV through a basic ion exchange resin, conveniently in a column. The product may be precipitated and worked-up as described above.

The synthesis may be carried out at temperatures within a wide range, generally from $-10°$ to $40°$ C. The time taken for the reaction to go substantially to completion may be from 5 minutes to overnight. Preferably the reaction is carried out at ambient temperature, and is usually complete in about 1 hour. The products should be crystallized from their solutions at ambient temperature without heating.

The invention is illustrated by the following Examples.

EXAMPLE 1

(a) Preparation of Starting Material

To a solution of 7-chloro-2-methylamino-5-phenyl-3H-1,4-benzodiazepine-4-oxide hydrochloride (33.6 g) in water (400 ml) in a 1 liter round-bottomed flask equipped with a magnetic stirrer was added concentrated hydrochloric acid (11 ml) and 40% formalin (20 ml). The flask was stoppered and stirred for 60 hrs. at room temperature (15° to 20° C). The precipitated solid was filtered, washed with water (2×25 ml) and air dried. Crystallization from a mixture of methanol and ether yield 27 g 7-chloro-1-hydroxymethyl-2-(N-methyl-N-hydroxymethyl)amino-5-phenyl-1H-1,4-benzodiazepine-4-oxide hydrochloride, melting at 189° to 190° C (with decomposition).

(b) Preparation of 1,5-Benzodiazocine Compound

To a solution of the 7-chloro-1-hydroxymethyl-2-(N-methyl-N-hydroxymethyl-amino)-5-phenyl-1H-1,4-benzodiazepine-4-oxide hydrochloride (4 g) in ethanol (150 ml) in a 500 ml beaker equipped with a magnetic stirrer was added dropwise 10% aqueous sodium hydroxide (10 ml) and the mixture was stirred for a period of half an hour. It was diluted with water (150 ml) and stirred for a further ½ hour. The precipitated product was filtered and washed well with water until washings were free from alkali, then twice with 20 ml portions of ethanol and dried to constant weight. The yield of 8-chloro-2-methylamino-6-phenyl-1,5-benzodiazocine-5-oxide was 2.9 g. The product had the appearance of colourless crystals, M.P. 204° to 205° C (with decomposition). Analysis of the product gave the following results:

Calculated for $C_{17}H_{14}ClN_3O$: C=65.5%, H=4.5%, N=13.5%. Found: C=65.2%, H=4.6%, N=13.4%.

EXAMPLE 2

4 g of 7-chloro-1-hydroxymethyl-2-(N-methyl-N-hydroxymethyl-amino)-5-phenyl-1H-1,4-benzodiazepine-4-oxide hydrochloride, prepared in the manner of Example 1(a) (starting material preparation) was triturated in a mortar with 50 ml of aqueous ammonia for ½ hour. The product was filtered, washed well with water until the washings were free from alkali, then twice with 20 ml portions of ethanol and dried to constant weight. The yield of 8-chloro-2-methylamino-6-phenyl- 1,5-benzodiazocine-5-oxide was 1.9 g. The product had the appearance of colourless crystals, M.P. 204° to 205° C (with decomposition).

EXAMPLE 3

(a) Preparation of Starting Material

To a solution of 7-chloro-2-methylamino-5-phenyl-3H-1,4-benzodiazepine-4-oxide hydrochloride (33.6 g) in water (400 ml) in a 500 ml round-bottomed flask, equipped with a magnetic stirrer, was added concentrated HCl (11 ml) and acetaldehyde (8.25 ml). The flask was stoppered and stirred slowly for 60 hrs. at room temperature (15° to 20° C). The precipitated solid was filtered, washed with water (2×25 ml) pressed well and air dried. It was crystallized from methanol and ether to obtain colourless crystals M.P. 170° to 171° C (with decomposition). The yield was 15 g of 7-chloro-2-(N-methyl-N-1-hydroxyethylamino)-5-phenyl-3H-1,4-benzodiazepine-4-oxide hydrochloride.

(b) Preparation of 1,5-benzodiazepine Compound

To a solution of the 7-chloro-2-(Nmethyl-N-1-hydroxyethyl-amino)-5-phenyl-3H-1,4-benzodiazepine-4-oxide hydrochloride (1.9 g) in 30 ml of 1,2-dimethoxyethane was added dropwise 10% aqueous sodium hydroxide (5 ml) and the mixture was stirred for ½ hour, diluted with water (100 ml) and stirred for a further 15 minutes. The product was filtered, washed well with water and crystallised from ethyl acetate. The yield of 8-chloro-4-methyl-2-methylamino-6-phenyl-1,5-benzodiazocine-5-oxide was 500 mg, M.P. 178° to 179° C. Analysis of the product gave the following results:

Calculated for $C_{18}H_{16}ClN_3O$: C=66.4%, H=4.9%, N=12.9%. Found: C=66.0%, H=5.0%, N=12.8%.

EXAMPLE 4

(a) Preparation of Starting Material

The preparative method of Example 3(a) for starting material was repeated except that propionaldehyde (10.9 ml) was used in place of the acetaldehyde. There was obtained 17.1 g of 7-chloro-2-(N-methyl-N-1-hydroxypropyl-amino)-5-phenyl-3H-1,4-benzodiazepine-4-oxide-hydrochloride, melting at 194° to 195° C with decomposition.

(b) Preparation of 1,5-Benzodiazocine Compound

To a solution of the 7-chloro-2-(N-methyl-N-1-hydroxypropyl-amino)-5-phenyl-3H-1,4-benzodiazepine-4-oxide hydrochloride (3.94 g) in methanol (100 ml) was added, dropwise with stirring, 10% aqueous sodium hydroxide (10 ml) and the mixture was stirred for ½ hour and then diluted with water (250 ml). The precipitated product was filtered and washed well with water until the washings were free from alkali. The product was carefully air dried and crystallized at room temperature from diethyl ether. The yield of yellowish crystals of 8-chloro-4-ethyl-2-methylamino-6-phenyl-1,5-benzodiazocine-5-oxide was 1.8 g, M.P. 150° to 152° C. Analysis of the product gave the following results:

Calculated for $C_{19}H_{18}ClN_3O$: C=67.2%, H=5.3%, N=12.4%.

EXAMPLE 5

A strongly basic ion-exchange column was prepared as follows:

40 g of Amberlite (Trade Mark) IR-400 (Cl⁻) was kept overnight in 100 ml 2N HCl. It was transferred into a glass chromatographic column and covered with a plug of cotton wool. It was washed with water until it was free from chloride ions. The base was generated by passing 100 ml 1N sodium hydroxide solution at a rate of 2 ml/min. Then the column was washed with water until it was free from sodium ions, and was washed further with 100 ml methanol. Then a solution of the 7-chloro-2-(N-methyl-N-1-hydroxypropyl-amino)-5-phenyl-3H-1,4-benzodiazepine-4-oxide hydrochloride of Example 4(a) (394 mg), in 100 ml methanol, was passed through the column at the rate of 2 ml/min. The eluted methanolic solution was taken up in 250 ml water and the product was filtered and crystallized from ether. The yield of yellowish crystals of 8-chloro-4-ethyl-2-methyl-amino-6-phenyl-1,5-benzodiazocine-5-oxide was 90 mg. M.P. 148° to 150° C.

EXAMPLE 6

(a) Preparation of Starting Material

The preparative method of Example 3(a) for starting material was repeated except that n-butyraldehyde (13.5 ml) was used in place of the acetaldehyde. There was obtained 18 g of 7-chloro-2-(N-methyl-N-1-hydroxybutyl-amino)-5-phenyl-3H-1,4-benzodiazepine-4-oxide hydrochloride, melting at 199° to 200° C with decomposition.

(b) Preparation of 1,5-Benzodiazocine Compound

Example 4(b) was repeated using the 7-chloro-2-(N-methyl-N-1-hydroxybutyl-amino)-5-phenyl-3H-1,4-benzodiazepine-4-oxide hydrochloride (4.08 g) as starting material, and there was obtained 1 g of yellowish crystals of 8-chloro-4-propyl-2-methylamino-6-phenyl-1,5-benzodiazocine-5-oxide. M.P. 104° to 106° C Analysis of the product gave the following results:

Calculated for $C_{20}H_{20}ClN_3O$: C=67.9%. H=5.7%, N=11.9%. Found: C=67.9%, H=5.9%, N=11.6%.

EXAMPLE 7

Example 4(b) was repeated using the 7-chloro-2-(N-methyl-N-1-hydroxyethyl-amino)-5-phenyl-3H-1,4-benzodiazepine-4-oxide hydrochloride (1.9 g) of Example 3(a) as starting material, and there was obtained 1.2 g of colourless crystals of the methanol solvate of 8-chloro-4-methyl-2-methylamino-6-phenyl-1,5-benzodiazocine-5-oxide, M.P. 128° to 130° C. Analysis of the product gave the following results:

Calculated for $C_{19}H_{20}ClN_3O_2$: C=63.8% H=5.6%, N=11.8%. Found: C=63.6% H=5.5%, N=11.7%.

EXAMPLE 8

Example 7 was repeated using ethanol as the solvent, and the product was stirred with ethanol in a mortar. There was obtained 0.9 g of colourless crystals of the ethanol solvate of 8-chloro-4-methyl-2-methylamino-6-phenyl-1,5-benzodiazocine-5-oxide, M.P. 120° to 122° C. Analysis of the product gave the following results:

Calculated for $C_{20}H_{22}N_3ClO_2$: C=64.6%, H=5.9%, N=11.3%. Found: C=64.2%, H=5.9%, N=11.0%.

EXAMPLE 9

Example 7 was repeated using isopropyl alcohol as the solvent and there was obtained 1.1g of colourless crystals of the isopropanol solvate of 8-chloro-4-methyl-2-methylamino-6-phenyl-1,5-benzodiazocine-5-oxide, M.P. 120° to 122° C. Analysis of the product gave the following results:

Calculated for $C_{21}H_{24}N_3ClO_2$: C=65.4%, H=6.2%, N=10.9%. Found: C=65.1%, H=6.2%, N=10.9%.

EXAMPLE 10

Example 5 was repeated using the 7-chloro-2-(N-methyl-N-1-hydroxyethyl-amino)-5-phenyl-3H-1,4-benzodiazepine-4-oxide hydrochloride (380 mg) of Example 3 (a) as starting material and there was obtained 75 mg of colourless crystals of the methanol solvate of 8-chloro-4-methyl-2-methylamino-6-phenyl-1,5-benzodiazocine-5-oxide, M.P. 128° C.

EXAMPLE 11

(a) Preparation of starting Material

To a solution of 7-chloro-2-methylamino-5-phenyl-3H-1,4-benzodiazepine-4-oxide hydrochloride (16.8 g) in water (200 ml) was added propionaldehyde (5.5 ml) and the mixture was stirred for three days at room temperature. Methylene dichloride (100 ml) was added to the resulting solution and the mixture was stirred for a further 6 hours. A precipitate formed and was removed by filtration after standing overnight. The precipitate was washed with water (2 × 10 ml) and recrystallized from a methanol, diethyl ether, petroleum ether mixture. The yield was 5 g of 2-(N-methyl-N-hydroxypropyl-aminomethyl)-4-phenyl-6-chloro-quinazoline-3-oxide hydrochloride, M.P. 202°-3° C (with decomposition).

(b) Preparation of 1,5-Benzodiazocine Compound

To a solution of the 2-(N-methyl-N-1-hydroxypropyl-aminomethyl)-4-phenyl-6-chloro-quinazoline-3-oxide hydrochloride (1 g) in methanol (25 ml) was added with stirring 10% aqueous sodium hydroxide (2.5 ml) and the mixture was stirred for ½ hour. It was diluted with water (50 ml) and the product was filtered and crystallised from diethyl ether, which yielded 400 mg of pale yellowish crystals of 8-chloro-4-ethyl-2-methylamino-6-phenyl-1,5-benzodiazocine-5-oxide, M.P. 145° to 147° C.

EXAMPLE 12

(a) Preparation of Starting Material

Example 11(a) was repeated using n-butyraldehyde (6.75 ml) in place of the propionaldehyde. There was obtained 1 g of 2-(N-methyl-N-hydroxybutyl-aminomethyl)-4-phenyl-6-chloro-quinazoline-3-oxide hydrochloride, melting at 193° to 194° C with decomposition.

(b) Preparation of 1,5-Benzodiazocine Compound

To a solution of the starting material (1 g) in methanol (25 ml) was added with stirring concentrated aqueous ammonia (2.5 ml) and the mixture was stirred for ½ hour. It was diluted with water (50 ml) and the product was filtered and crystallized from diethyl ether and hexane to yield 360 mg of yellowish crystals of 8-chloro-4-propyl-2-methylamino-6-phenyl-1,5-benzodiazocine-5-oxide, M.P. 104° tp 106° C.

EXAMPLE 13

(a) Preparation of Starting Material

Example 11(a) was repeated using acetaldehyde (4.1 ml) in place of the propionaldehyde. There was obtained 1.4 g of 2-(N-methyl-N-hydroxyethyl-aminomethyl)-4-phenyl-6-chloro-quinazoline-3-oxide hydrochloride, melting at 196° to 197° C with decomposition.

(b) Preparation of 1,5-Benzodiazocine Compound

To a solution of the starting material (0.950 g) in 20 ml 1,2-dimethoxyethane was added 1,2-dimethoxyethane was added 10% aqueous sodium hydroxide (2.5 ml) and the mixture was stirred for ½ hour and diluted with water (60 ml). The precipitated product was filtered and crystallised from ethyl acetate to obtain 300 mg of pale yellowish crystals of 8-chloro-4-methyl-2-methylamino-6-phenyl-1,5-benzodiazocine-5-oxide, M.P. 178° to 179° C.

EXAMPLE 14

Example 5 was repeated using 380 mg of 2-(N-methyl-N-1-hydroxyethyl-aminomethyl)-4-phenyl-6-chloro-quinazoline-3-oxide hydrochloride of Example 13(a) as starting material, and there was obtained 120 mg of colourless crystals of the methanol solvate of 8-chloro-4-methyl-2-methylamino-6-phenyl-1,5-benzodiazocine-5-oxide, M.P. 128° to 130° C.

EXAMPLE 15

Example 5 was repeated using 394 mg of 2-(N-methyl-N-1-hydroxypropyl-aminomethyl)-4-phenyl-6-chloro-quinazoline-3-oxide hydrochloride of Example 11(a) as starting material. There was obtained 100 mg of yellowish crystals of 8-chloro-4-ethyl-2-methylamino-6-phenyl-1,5-benzodiazocine-5-oxide, M.P. 147° to 149° C.

EXAMPLE 16

Example 5 was repeated using 408 mg of 2-(N-methyl-N-1-hydroxybutyl-aminomethyl)-4-phenyl-6-chloro-quinazoline-3-oxide hydrochloride of Example 12(a) as starting material. There was obtained 60 mg of 8-chloro-4-propyl-2-methylamino-6-phenyl-1,5-benzodiazocine-5-oxide, M.P. 104° to 106° C.

EXAMPLE 17

Example 5 was repeated using 408 mg of 7-chloro-2-(N-methyl-N-hydroxybutyl-amino)-5-phenyl-3H-1,4-benzodiazepine-4-oxide hydrochloride of Example 6(a) as starting material and there was obtained 45 mg of 8-chloro-4-propyl-2-methylamino-6-phenyl-1,5-benzodiazocine-5-oxide, M.P. 104° to 106° C.

What I claim is:

1. A 1,5-Benzodiazepine derivative of the general formula

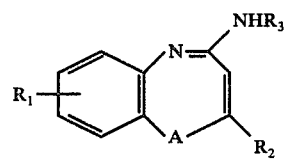

wherein $R_1$ represents chlorine, a trifluoromethyl, cyano or nitro all in the 8 position; $R_2$ represents a hydrogen atom or a lower alkyl group; $R_3$ represents a hydrogen atom, a lower alkyl group, a hydroxy group, a lower alkenyl group or a benzyl group;

and A represents a grouping of the general formula

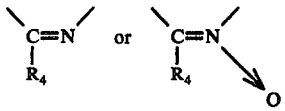

in which $R_4$ represents a phenyl, (lower alkyl) phenyl, nitrophenyl or halophenyl; or a pharmaceutically acceptable acid addition salt thereof.

2. A compound according to claim 1 wherein $R_3$ is methyl and $R_4$ is phenyl.

3. 8-chloro-2-methylamino-6-phenyl-1,5-benzodiazocine-5-oxide.

4. 8-chloro-4-methyl-2-methylamino-6-phenyl-1,5-benzodiazocine-5-oxide or a solvate thereof with methanol, ethanol or isopropanol.

5. 8-chloro-4-ethyl-2-methylamino-6-phenyl-1,5-benzodiazocine-5-oxide.

6. 8-chloro-4-propyl-2-methylamino-6-phenyl-1,5-benzodiazocine-5-oxide.

7. An acid addition salt of a compound of claim 1 with a pharmaceutically acceptable inorganic or organic acid.

8. 8-chloro-2-methylamino-6-phenyl-1,5-benzodiazocine-5-oxide hydrochloride.

9. 8-chloro-4-methyl-2-methylamino-6-phenyl-1,5-benzodiazocine-5-oxide hydrochloride.

10. 8-chloro-4-ethyl-2-methylamino-6-phenyl-1,5-benzodiazocine-5-oxide hydrochloride.

11. 8-chloro-4-pyropyl-2-methylamino-6-phenyl-1,5-benzodiazocine-5-oxide hydrochloride.

12. A solvate according to claim 4.

13. A tranquilizing, sedative or hypnosis-inducing composition comprising a tranquilizing, sedative, or hypnosis-inducing amount of at least one compound according to claim 1 in admixture with a pharmacologically acceptable diluent or carrier.

* * * * *

UNITED STATES PATENT AND TRADEMARK OFFICE
CERTIFICATE OF CORRECTION

PATENT NO. : 4,089,953

DATED : May 16, 1978

INVENTOR(S) : Umakant Devdas Shenoy

It is certified that error appears in the above-identified patent and that said Letters Patent are hereby corrected as shown below:

Column 1, lines 24-29, lines leading to "A" in the formula should be inserted.

Column 2, line 43, "be" should read -- by --.

Column 2, lines 27-34, lines leading to "A" in the formula should be inserted.

Column 2, lines 46-54, lines leading to "A" in the formula should be inserted.

Column 2, lines 61-67, lines leading to "A" in the formula should be inserted.

Column 3, line 24, lines leading to "A" in the formula should be inserted.

Column 5, line 22, "Nmethyl" should read -- N-methyl --.

Column 7, line 59, "tp" should read -- to --.

UNITED STATES PATENT AND TRADEMARK OFFICE
CERTIFICATE OF CORRECTION

PATENT NO. : 4,089,953

DATED : May 16, 1978

INVENTOR(S) : Umakant Devdas Shenoy

It is certified that error appears in the above—identified patent and that said Letters Patent are hereby corrected as shown below:

Column 10, line 12, "pyropyl" should read -- propyl --.

Signed and Sealed this

Twenty-first Day of November 1978

[SEAL]

Attest:

RUTH C. MASON
*Attesting Officer*

DONALD W. BANNER
*Commissioner of Patents and Trademarks*